United States Patent [19]
Imai et al.

[11] Patent Number: 5,742,332
[45] Date of Patent: Apr. 21, 1998

[54] VIEWING-POSITION TRACKING STEREOSCOPIC DISPLAY

[75] Inventors: Hiroshi Imai; Masao Imai, both of Tokyo, Japan

[73] Assignee: NEC Corporation, Tokyo, Japan

[21] Appl. No.: 652,739

[22] Filed: May 23, 1996

[30] Foreign Application Priority Data

May 26, 1995 [JP] Japan ................................. 7-128046

[51] Int. Cl.$^6$ ............................ A04H 13/00; A04H 5/225
[52] U.S. Cl. ................................ 348/51; 348/42; 348/169
[58] Field of Search ......................... 348/42, 169, 170, 348/171, 172, 51, 53, 54; 364/516, 550; 351/210, 226; 396/51

[56] References Cited

U.S. PATENT DOCUMENTS

| | | | |
|---|---|---|---|
| 3,986,030 | 10/1976 | Teltscher | 250/349 |
| 4,109,145 | 8/1978 | Graf | 250/201 |
| 4,648,052 | 3/1987 | Friedman et al. | 364/550 |
| 4,973,149 | 11/1990 | Hutchinson | 351/210 |
| 5,170,153 | 12/1992 | Migozzi et al. | 340/705 |
| 5,220,361 | 6/1993 | Lehmer et al. | 351/226 |
| 5,583,795 | 12/1996 | Smyth | 364/516.44 |

OTHER PUBLICATIONS

Japanese patent application entitled "Three Dimensional Image Display" by Hirauchi, Prov. Pub. No. 107247/89.

*Primary Examiner*—Amelia Au
*Assistant Examiner*—David R. Vincent
*Attorney, Agent, or Firm*—Laff, Whitesel, Conte & Saret, Ltd.

[57] ABSTRACT

The invention tracks an observer's viewing-position correctly. The viewing-position is subject to shifting swiftly in a viewing-position tracking stereoscopic-display having a time delay of the viewing-position tracking from movement of the observer's viewing-position. A viewing-position tracking stereoscopic-display includes a viewing-position sensor, first and second order differentiators for differentiating positional information of the observer's viewing-position. Gain multipliers multiply the outputs of the differentiators. Band pass filters filter the outputs of the gain multipliers. A viewing-position tracker is driven by a viewing-position tracker driver according to the positional information compensated by adding the outputs of the band pass filters. A liquid crystal projector mounted on the viewing-position tracker projects parallactical images on a lenticular screen tracking the viewing-position, compensated for the time delay, representing a stereoscopic-view of good quality even when the viewing-position of the observer is shifted swiftly.

9 Claims, 8 Drawing Sheets

(When there is no error.)

FIG. 5(b)

(When there is a tracking error.)

VIEWING-POSITION TRACKING STEREOSCOPIC DISPLAY

BACKGROUND OF THE INVENTION

This invention relates to a viewing-position tracking stereoscopic display and a method of viewing-position tracking applied therein, which enables an observer to enjoy a stereoscopic view from a desired position without any special eyeglasses.

Various approaches are studied concerning stereoscopic display inspired by a recent rising demand for a stereoscopic presentation.

These days, attention is paid especially to a project type stereoscopic display which realizes a stereoscopic view by presenting each of two images having binocular parallax to each of two eyes by way of a lenticular screen, having a merit of needing no special eyeglass.

Figure 6:
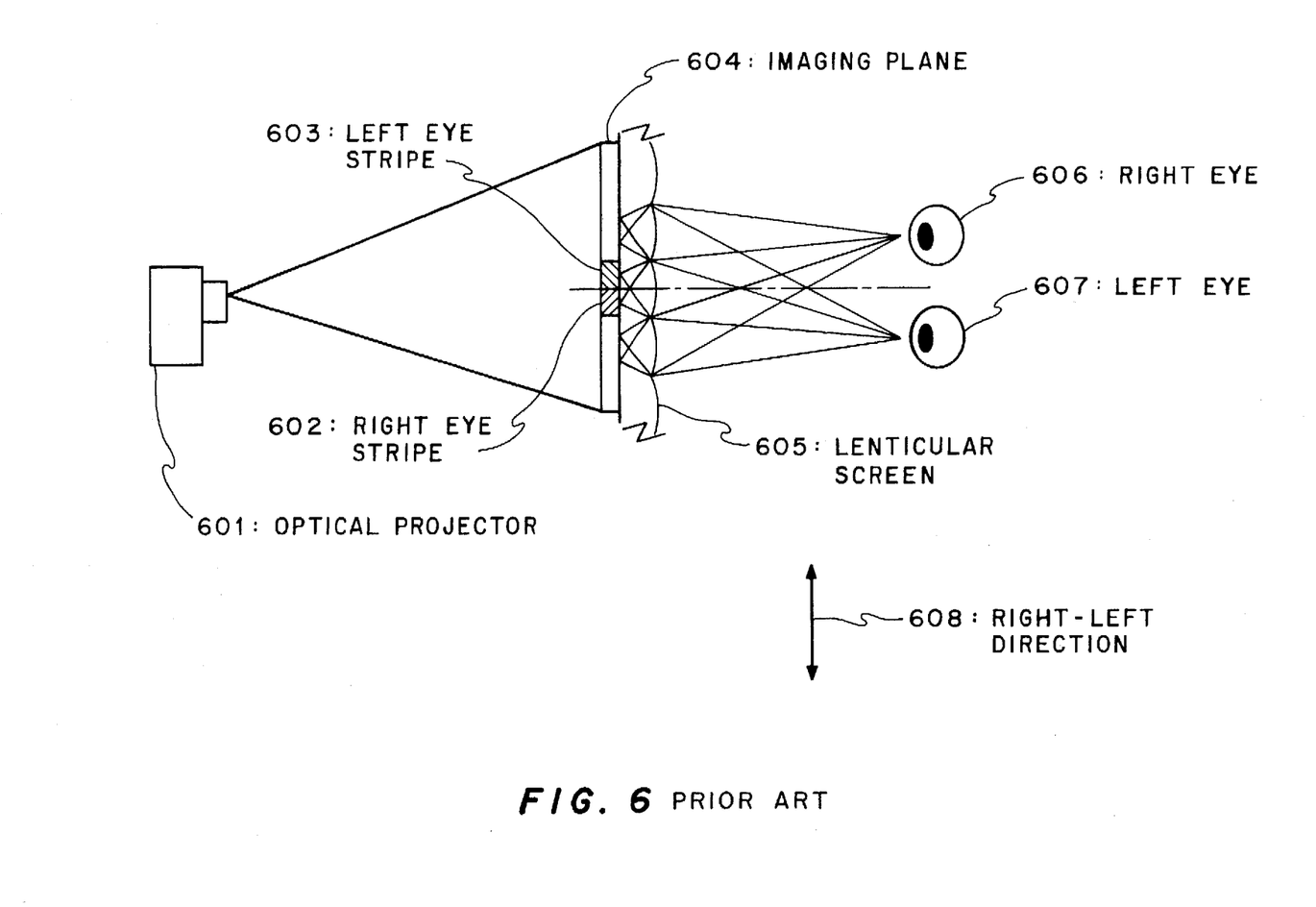
FIG. 6 is a plane view illustrating a conventional project type stereoscopic display with a lenticular screen.

FIG. 6 is a plane view illustrating a conventional project type display with a lenticular screen consisting of a number of columns of cylindrical lenses. On a focal plane of the cylindrical lenses, an optical projector 601 projects an image composed of stripes divided of a right eye view and a left eye view and ranged in turn cyclically. In FIG. 6, there are illustrated slender stripes long in a direction perpendicular to the paper ranged in a right and left direction 608. An observer perceives a stereoscopic view with images having a parallax, since view lines of the observer's right eye 606 and left eye 607 insert the lenticular screen with different angles. In FIG. 6, the parallactical images are illustrated simplified to a right eye stripe 602 and a left eye stripe 603.

In the project type stereoscopic display described with a lenticular screen, there is a problem that areas from where the observer can perceive stereoscopic view are dispersed discretely, especially width of the areas in the right and left direction 608 being limited within a distance between both eyes.

Figure 7:
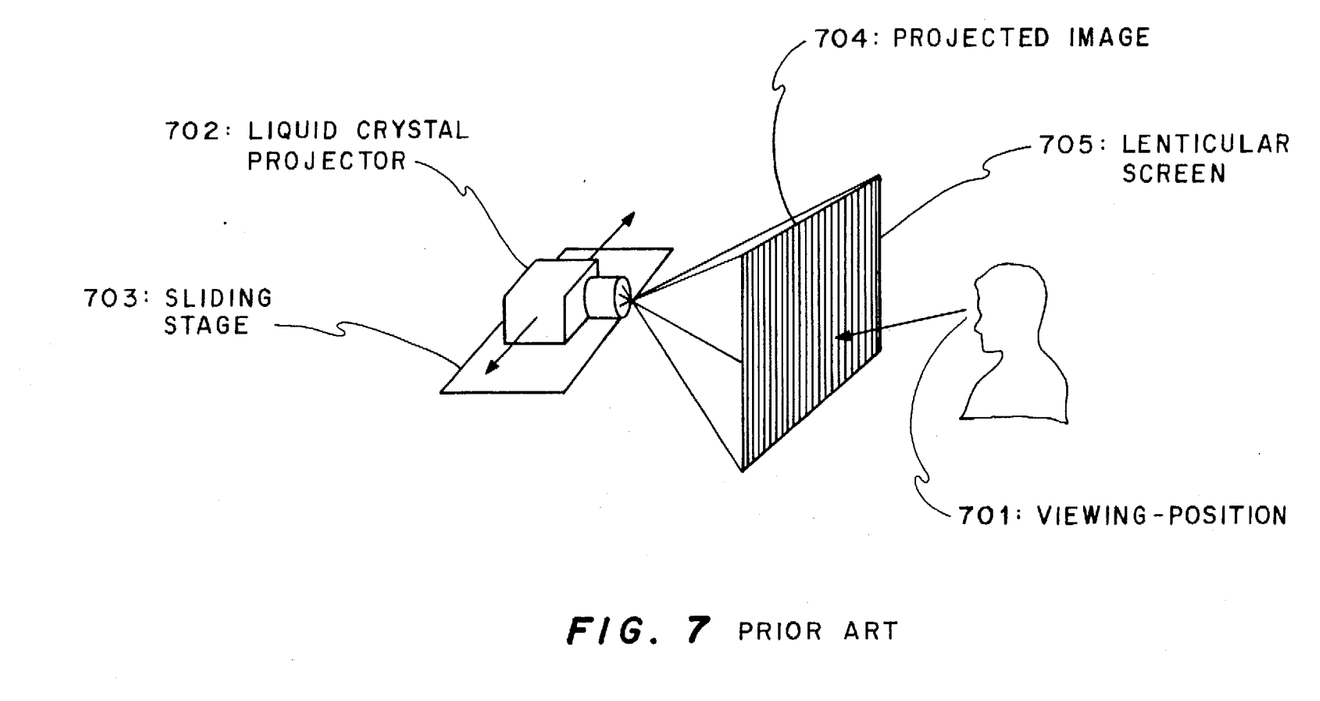
FIG. 7 illustrates a conventional viewing-position tracking stereoscopic display with a lenticular screen.

So, in order to enlarge the right and left width of the areas enjoyable of the stereoscopic images, there is disclosed, in a Japanese patent application laid open as a Provisional Publication No. 107247/'89 as an example, a viewing position tracking stereoscopic display always controlling a projecting position of the parallactical images according to observer's detected viewing-position. As used herein, the term "viewing-position" means the horizontal position, parallel to the display screen, at the center between the two eyes of the observer, and on his brow line. The prior art is illustrated in a perspective view of FIG. 7, wherein a liquid crystal projector 702 is applied. A projected image 704 on a lenticular screen 705 is adjusted right and left according to movement of an observer's viewing-position 701 by controlling a sliding stage 703 mounting the liquid crystal projector 702.

However, in the conventional viewing-position tracking stereoscopic display of the lenticular system, there is immanent a problem that it can not present a stereoscopic view correctly when the observer shifts his eyes swiftly because of an increase of error between the eye-point and the position of the parallactical images tracking it caused by time delays in the signal processing.

Figure 8A:
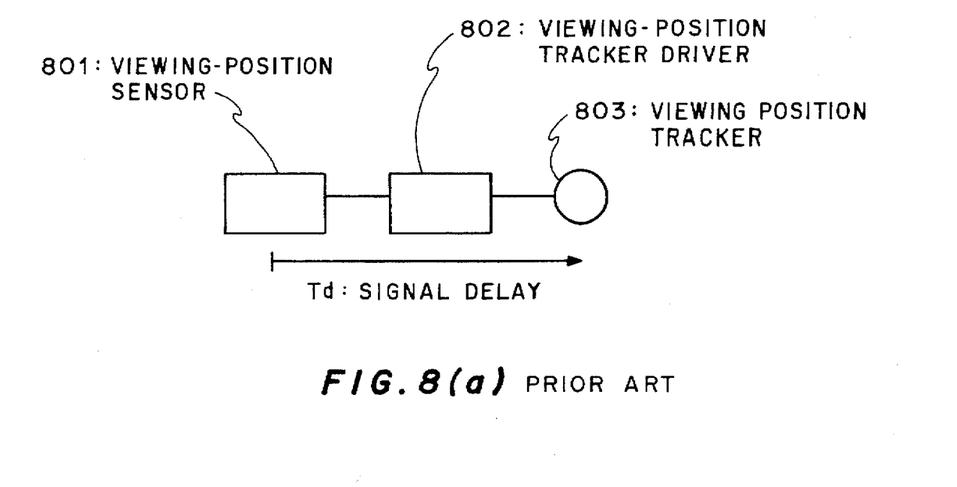
FIG. 8(a) is a block diagram showing a viewing-position tracking mechanism.
Figure 8B:
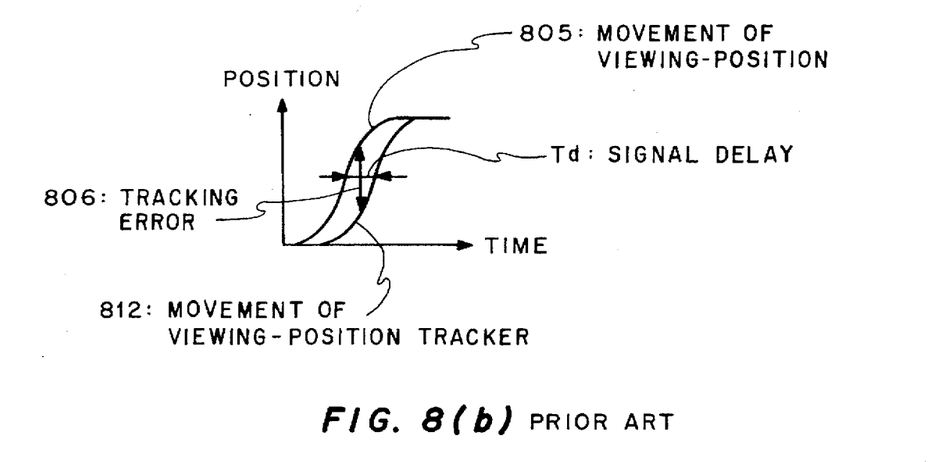
FIG. 8(B) illustrates relation between movements of observer's eyes and the viewing-position tracker.
Figure 8C:
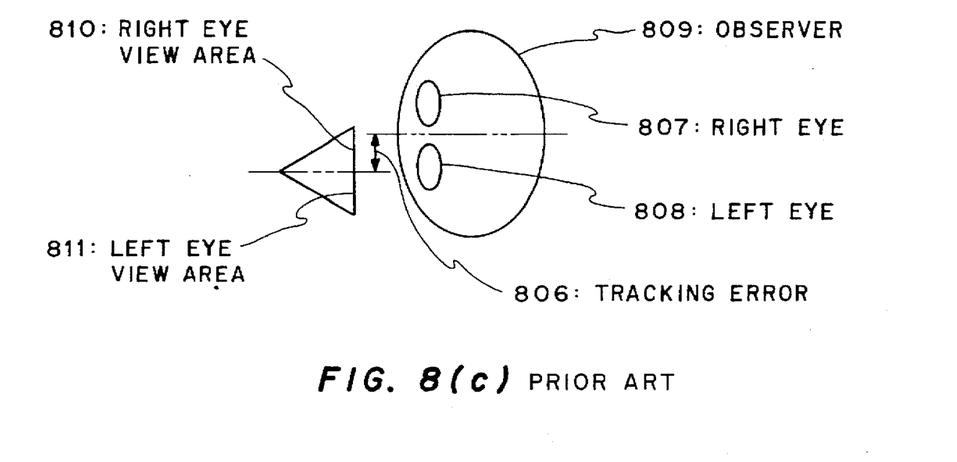
FIG. 8(c) illustrates relation between the observer's eyes and view areas of the parallactical images tracking them.

The problem is described referring to FIGS. 8(a) to 8(c).

FIG. 8(a) is a block diagram showing a viewing position tracking mechanism, wherein a signal delay $T_d$ is caused by data processing or data transfer in an sensor 801, an a viewing-position tracker driver 802 and an a viewing position tracker 803. Relation between movements of observer's eyes and the viewing-position tracker 802 is illustrated in FIG. 8(b). A tracking error 806 increases according to shifting speed of the observer's viewing-position because of the signal delay $T_d$. When the signal delay $T_d$ is 60 ms and the shifting speed of the observer's eyes is 30 cm/s, the tracking error 806 amounts to about 2 cm. FIG. 8(c) illustrates relation between the observer's viewing-position and the parallactical images tracking them. When the tracking error 806 increases, right and left eyes 807 and 808 of an observer 809 go out of corresponding view areas 810 and 811 of right and left eye. Therefore, it is difficult in the conventional stereoscopic display to perceive a stereoscopic view in a good condition when an observer shifts his viewing-position swiftly.

SUMMARY OF THE INVENTION

Therefore, a primary object of the invention is to provide a viewing-position tracking stereoscopic display and a method of viewing-position tracking applied therein, which can present a stereoscopic view correctly to an observer even when the observer shifts his eyes swiftly, by way of restricting the tracking error in an allowable limit by compensating delay time caused in signal processing for viewing-position tracking.

In order to achieve the object;

a viewing position tracking stereoscopic display of of an embodiment of the present invention having means for presenting right and left eye images separately to an observer, a viewing position sensor for detecting an eye-point of the observer, and a viewing position tracker for controlling the means for presenting according to output of the viewing-position sensor for representing a stereoscopic view to the observer whenever the viewing-position moves; comprises:

means for obtaining at least a first order differentiation of positional information of the eye-point of the observer to be used for controlling the viewing-position tracker after multiplied by delay time occurring in the viewing-position tracking stereoscopic display.

So, the tracking error, which was about 2 cm in the conventional method, can be reduced to 0.5 cm in the present invention, a quarter of the conventional method, on condition that the delay time is 60 ms and the viewing-position is shifted with a speed of 30 cm/s, enabling to present a stereoscopic view of a good quality even when the eye-point is shifted swiftly.

In another embodiment of the invention, the viewing-position tracking stereoscopic display further comprises;

means for revising a tracking error from the viewing-position tracker by comparing said positional information of the viewing-position of the observer with positional information fed-back of the viewing-position tracker.

Therefore, in the embodiment, the tracking error can be reduced to an eighth of the conventional method.

BRIEF DESCRIPTION OF THE DRAWINGS

The foregoing, further objects, features, and advantages of this invention will become apparent from a consideration of the following description, the appended claims, and the accompanying drawings in which the same numerals indicate the same or the corresponding parts.

DETAILED DESCRIPTION OF THE PREFERRED EMBODIMENTS

Now, embodiments of the present invention will be described in connection with the drawings.

Figure 1:
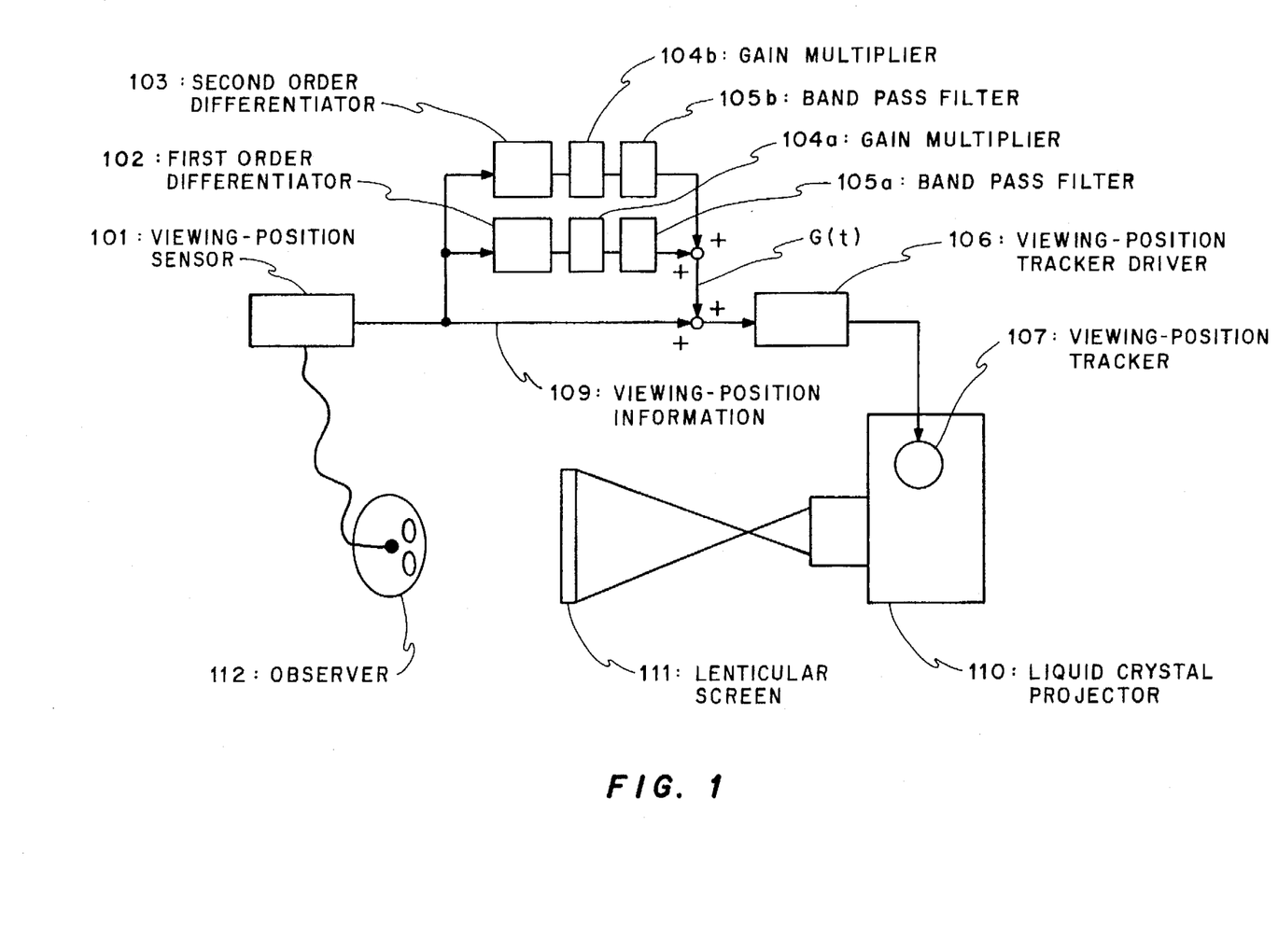
FIG. 1 is a block diagram illustrating a first embodiment of a viewing-position tracking stereoscopic display of the present invention.

FIG. 1 is a block diagram illustrating a first embodiment of a viewing-position tracking stereoscopic display of the present invention, comprising a viewing-position sensor 101, a first order differentiator 102, a second order differentiator 103, gain multipliers 104a and 104b, band pass filters 105a and 105b, tracker driver 106, a viewing-position tracker 107, a liquid crystal projector 110 and a lenticular screen 111.

The viewing-position of an observer is detected by the viewing-position sensor 101 and the viewing-position information 109 is differentiated by the fist order differentiator 102 and the second order differentiator 103. Both of the outputs are added to the viewing-position information 109 output of the viewing-position sensor 101 as a compensating value G(t) after processed through the gain multipliers 104a and 104b and the band pass filters 105a and 105b. The tracker driver 106 drives the viewing-position tracker 107 making use of the compensated information for tracking the observer's viewing-position. Here, the parallactical images are projected on the lenticular screen 111 by the liquid crystal projector 110 in the same way as in the prior art described.

Figure 2A:
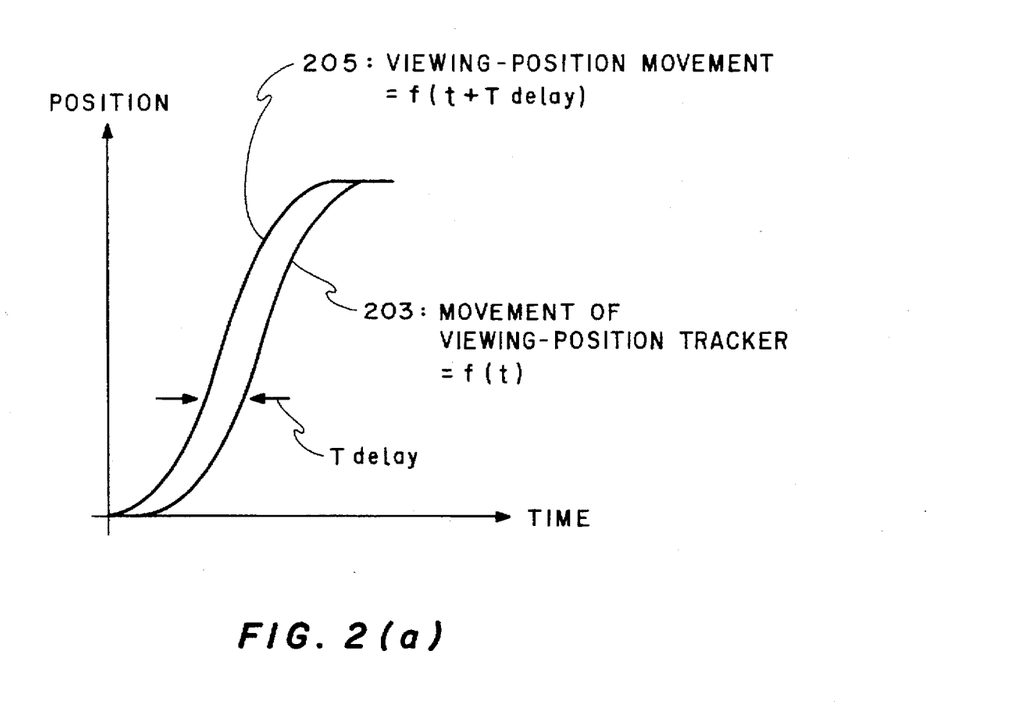
FIG. 2(a) is a graphic chart for illustrating principle of the first embodiment of the invention.

FIG. 2(a) is a graphic chart for illustrating principle of the first embodiment of the invention, showing a delay time $T_{delay}$ between viewing-position movement 205 of the observer's viewing-position and tracking movement 203 of the viewing-position tracker 106. Representing the tracking movement 203 by a function f(t), the viewing-position movement 205 advancing by the delay time $T_{delay}$ thereof is represented by a function $f(t+T_{delay})$ Taylor-expanded as following equation (1).

$$f(t+T_{delay}) = f(t) + f'(t)\frac{T_{delay}}{1!} + f''(t)\frac{(T_{delay})^2}{2!} + \ldots \quad (1)$$

Here, on condition that the delay time $T_{delay}$ is known and that the function f(t) is differentiable to n-th order, the function $f(t+T_{delay})$ can be approximated until (n+1)-th term in order to compensate effect of the delay time $T_{delay}$.

Figure 2B:
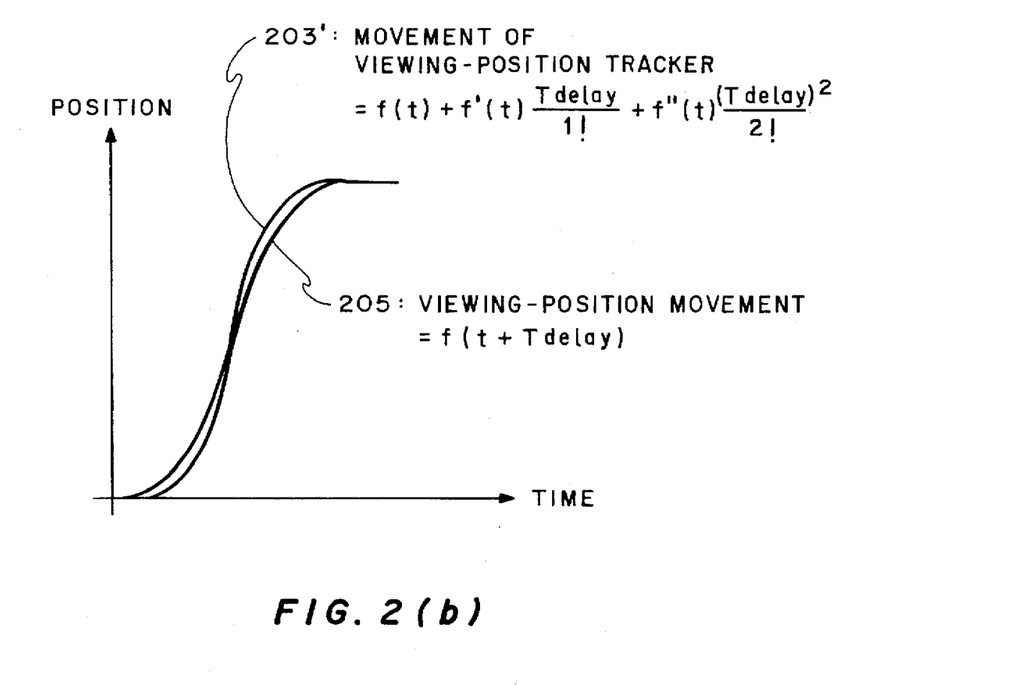
FIG. 2(b) shows an example of compensated tracking movement 203' approximating the viewing-position movement 205.

An example of compensated tracking movement 203' approximating the viewing-position movement 205 until the third term in the right side of the equation (1) is shown in FIG. 2(b), making the tracking error very small.

Method applied in the embodiment is described in the following paragraphs.

Referring to FIG. 1, the viewing-position of the observer is detected by the viewing-position sensor 101. The viewing-position information 109 detected by the viewing-position sensor 101 corresponds to the first term f(t) in right side of the equation (1). The viewing-position information 109 is supplied to the first order differentiator 102 for calculating first order differentiation f'(t) thereof. The output f'(t) of the first order differentiator 102 is input to the gain multiplier 104a wherein f'(t) is multiplied by the delay time $T_{delay}$. Thus an output $f'(t) \cdot T_{delay}$ corresponding to the second term in the right side of the equation (1) is obtained from the first order differentiator 102. In the same way, the viewing-position information 109 is input to the second order differentiator 103 for obtaining a second order differentiation f''(t) thereof, which is input to the gain multiplier 104b and multiplied with a value $(T_{delay})^2/2$. Thus an output $f''(t) \cdot (T_{delay})^2/2$ corresponding to the third term in the right side of the equation (1) is obtained from the second order differentiator 103. By adding the output $f'(t) \cdot T_{delay}$ of the first order differentiator 102 and the output $f''(t) \cdot (T_{delay})^2/2$ of the third order differentiator 103 to the viewing-position information 109, namely to f(t), as the compensating value G(t), an approximation of the equation (1) until the third term in the right side can be obtained.

By tracking the viewing-position of the observer eyes with the viewing-position tracker 107 driven by the viewing-position tracker driver 106 according to the compensated information, the effect of delay time $T_{delay}$ is suppressed enabling representation of a correct stereoscopic image.

In the embodiment, the band pass filter 105a or 105b is provided in each of the paths of differential information for decreasing noises therein. The first and the second order differentiators 102 and 103, the gain multipliers 104a and 104b and the band pass filters 105a and 105b are realized with digital signal processing in a computer.

With the method of viewing-position tracking above described, the tracking error, which was about 2 cm in the conventional method, is reduced to 0.5 cm, a quarter, on condition that the delay time is 60 ms and the viewing-position is shifted with a speed of 30 cm/s, enabling to present a stereoscopic view of a good quality even when the viewing-position is shifted swiftly.

Figure 3A:
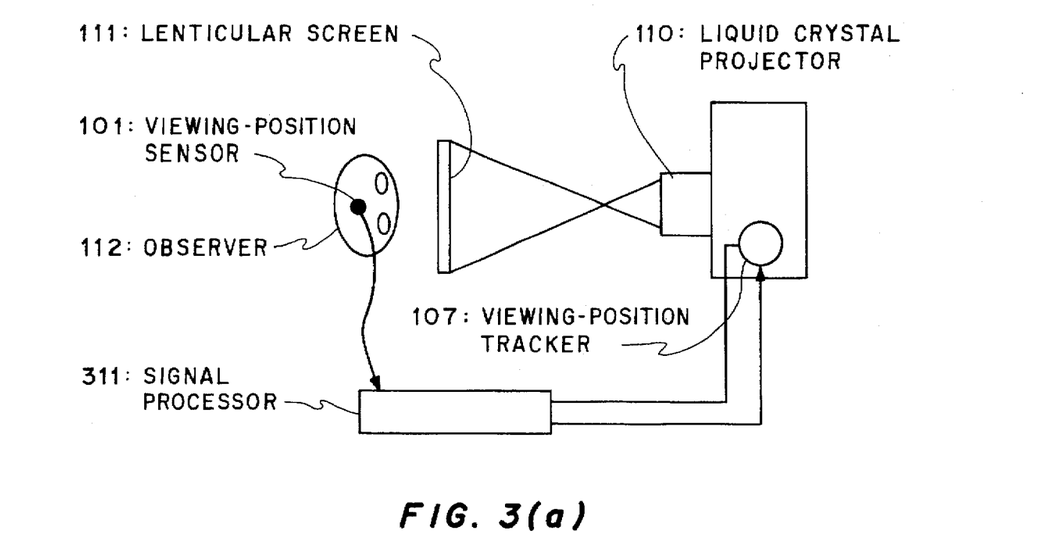
FIG. 3(a) illustrates a viewing-position tracking stereoscopic display of a second embodiment of the invention.
Figure 3B:
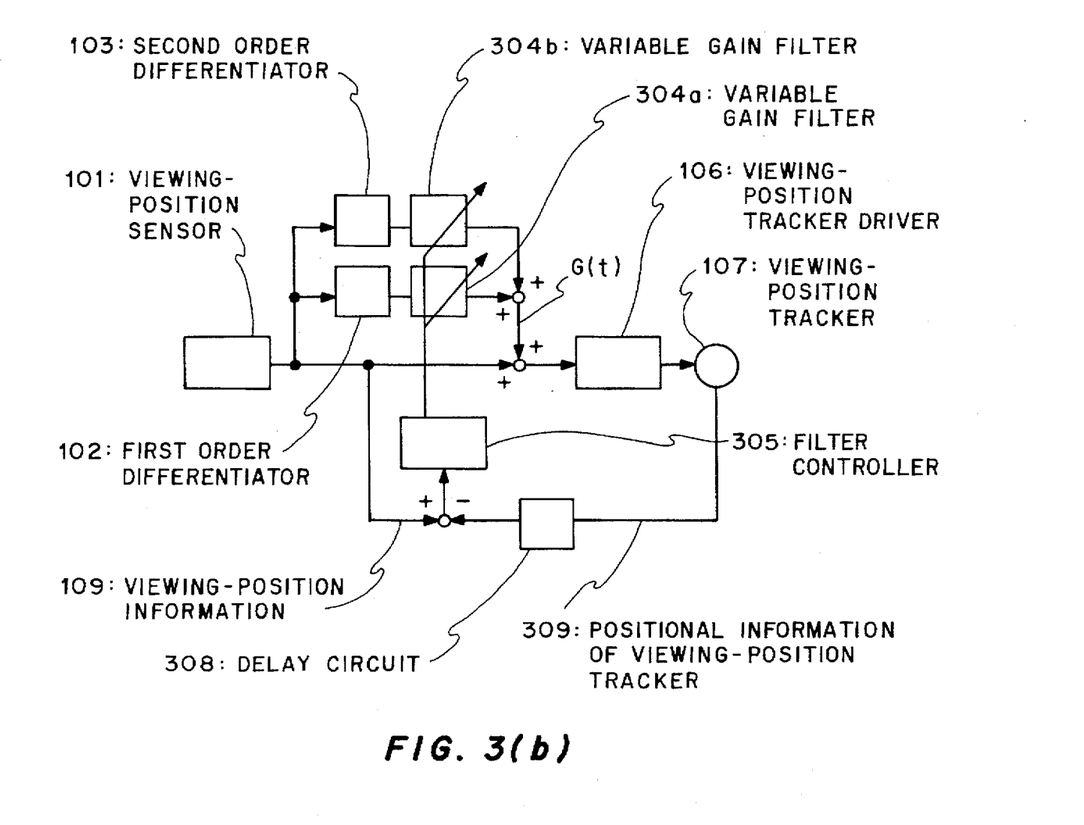
FIG. 3(b) illustrates block diagram of a signal processor 311 of FIG. 3(a) for viewing-position tracking.

FIG. 3(a) illustrates a viewing-position tracking stereoscopic display of a second embodiment of the invention comprising a signal processor 311 for viewing-position tracking, detail thereof illustrated in a block diagram of FIG. 3(b). The signal processor 311 has adaptation control means for feeding back positional information 309 of the eye-point tracker 307, which comprises a delay circuit 308 and a filter controller 305, in addition to the first embodiment of FIG. 1 and variable gain filters 304a and 304b replacing the gain multipliers and the band pass filters of FIG. 1.

In the second embodiment, at least first order differentiation of the viewing-position information 109 is added to the viewing-position information 109 itself, as same as in the first embodiment, for compensating for the effect of the delay time $T_{delay}$. And in addition, the variable gain filters 304a and 304b are controlled by the filter controller 305 in the second embodiment, so as to diminish the tracking error detected by comparing the positional information 309 with the viewing-position information 109.

Here, before the comparison, the positional information 309 is delayed through the delay circuit 308 to be compared with the viewing-position information 109 at the same time, since the viewing-position information 109 obtained from the sensor 101 has some delay from the actual movement of the observer viewing-position.

In the following paragraph, the method of viewing-position tracking in the second embodiment is described.

The delay time compensation is performed in the same way as in the first embodiment. And furthermore in the second embodiment, the variable gain filters 304a and 304b are controlled by the filter controller 305 so as to diminish the tracking error detected by comparison of the positional information fed-back from the viewing-position tracker 107 with the viewing-position information 109 obtained from the eye-point sensor 102.

When movement of the observer's viewing-position is decelerated, for example, a tracking error of overshooting occurs. In the case, the filter controller 305 reduces gain of the variable gain filter 304a outputting the first order differentiation and raises gain of the another variable gain filter 304b outputting the second order differentiation. Therefore, the second order differentiation of the viewing-position information 109, that is deceleration in the case, is emphasized for counteracting the overshoot, making the tracking error decreased.

Here, the first order differentiator 102, the second order differentiator 103, the delay circuit 308, the filter controller 305 and the variable gain filters 304a and 304b are realized with digital signal processing in a computer in the same way as in the first embodiment.

In the method of viewing-position tracking of the second embodiment above described, the tracking error, which was about 2 cm in the conventional method, is reduced to 0.25 cm, an eighth, on condition that the delay time is 60 ms and the viewing-position is shifted with a speed of 30 cm/s, enabling to present a stereoscopic view of a good quality even when the viewing-position is shifted swiftly.

Now a third embodiment of the invention is described.

Figure 4A:
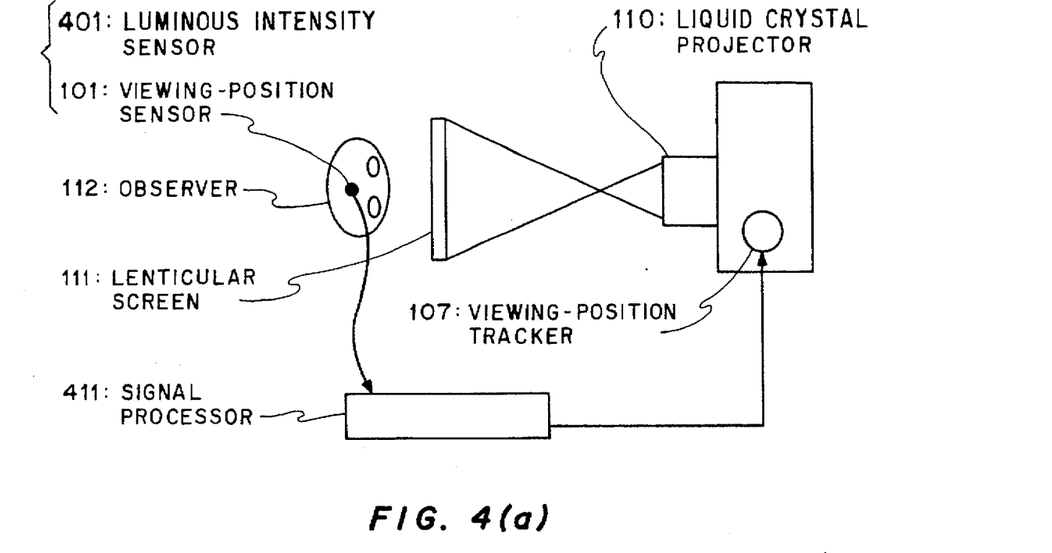
FIG. 4(a) illustrates a viewing-position tracking stereoscopic display of the third embodiment.
Figure 4B:
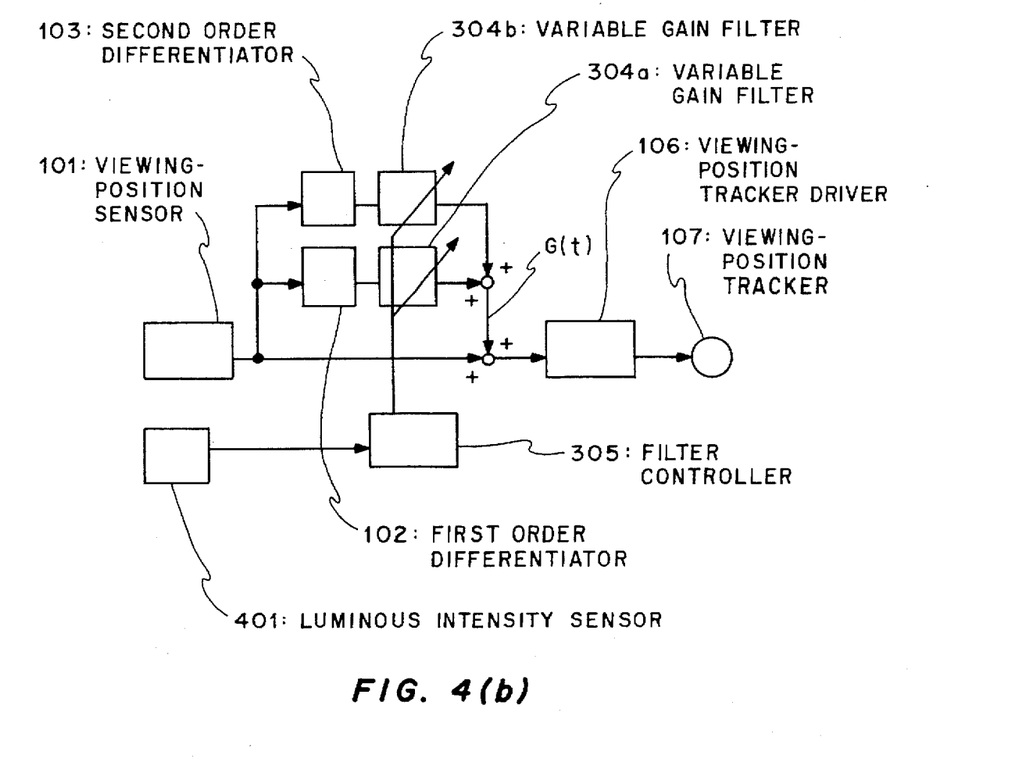
FIG. 4(b) illustrates block diagram of a signal processor 411 of FIG. 4(a) for viewing-position tracking.

FIG. 4(a) illustrates a viewing-position tracking stereoscopic display of the third embodiment comprising a signal processor 411 for viewing-position tracking, detail thereof illustrated in a block diagram of FIG. 4(b), wherein a luminous intensity sensor 401 is provided for detecting luminous intensity at the observer's head to be fed-back to the filter controller 305.

In the third embodiment, the delay time compensation and the tracking error reduction are performed similarly as in the second embodiment, but a difference lies in that the tracking error is measured directly by the luminous intensity sensor 401.

Figure 5A:
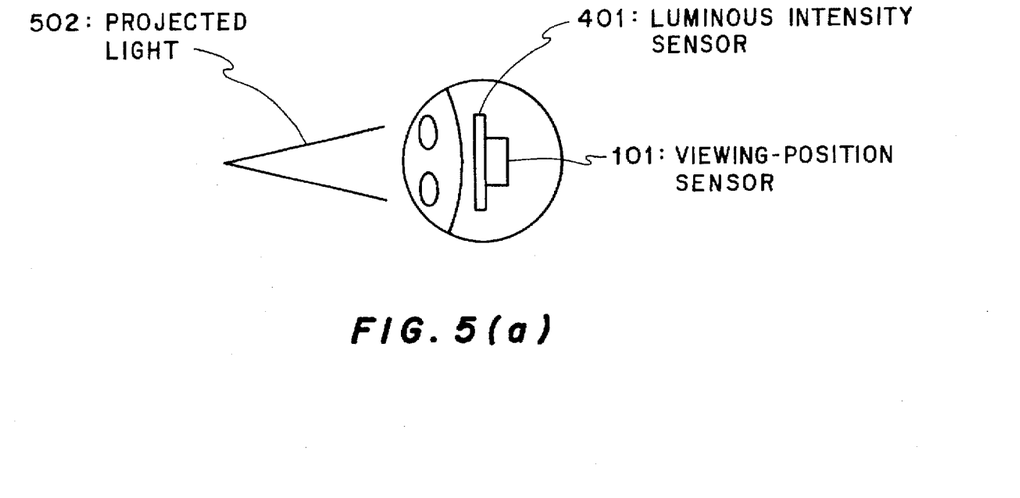
FIG. 5(a) illustrates a luminous intensity sensor 401 of FIG. 4(b).
Figure 5B:
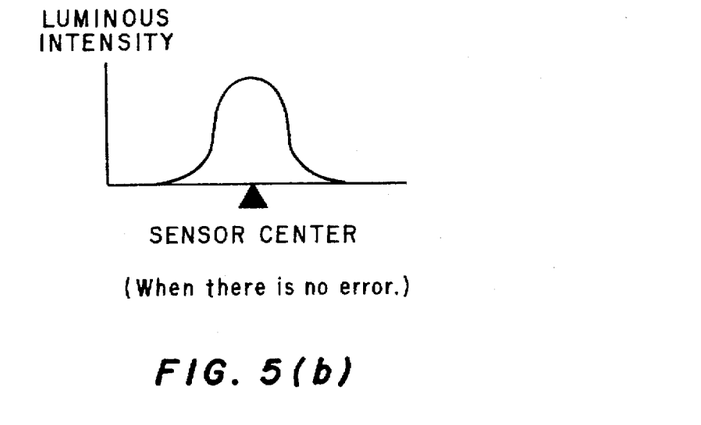
FIG. 5(b) is a graphic chart illustrating the maximum value of the luminous intensity at the center of the luminous intensity sensor 401 when there is no tracking error.
Figure 5C:
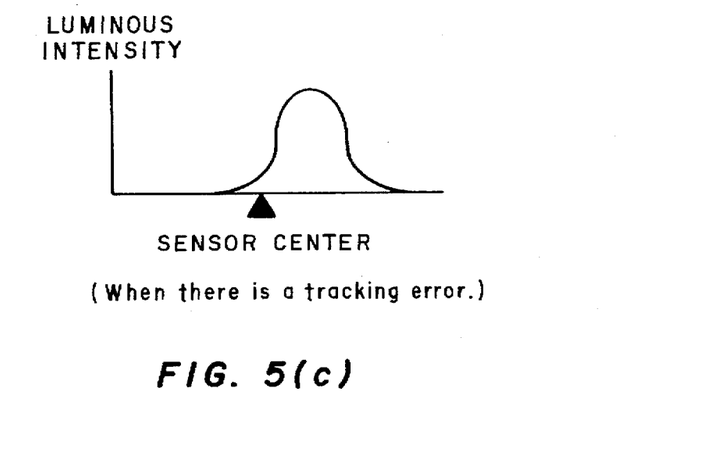
FIG. 5(c) is a graphic chart illustrating the maximum value of the luminous intensity shifted from the center of the luminous intensity sensor 401 in proportion to the tracking error.

Referring to FIG. 5(a) to FIG. 5(c), function of the luminous intensity sensor 410 is described. The luminous intensity sensor 401 is composed of a photo-diode array for detecting luminous intensity distribution in the right and left direction of the projected light 502 from the liquid crystal projector 110. So, when there is no tracking error, the luminous intensity sensor detects the maximum value of the luminous intensity at its center as shown in FIG. 5(b) and when a tracking error occurs, position of the maximum luminous intensity is shifted right or left in proportion to the tracking error as shown in FIG. 5(c).

Therefore, the filter controller 305 of the embodiment can control the variable gain filters 304a and 304b directly according to the output of the luminous intensity sensor 401, that is, when an overshoot error occurs because of a deceleration of the viewing-position movement, output of the first order differentiator 102 is attenuated and that of the second order differentiator 103 is amplified, for example.

Here also, the first differentiator 102, the second differentiator 103, the filter controller 305 and the variable gain filters 304a and 304b are realized with digital signal processing in a computer. And the tracking error can be reduced to an eighth of the conventional method as much as in the second embodiment in the same condition.

As for the luminous intensity sensor 410, a photo-diode array is applied in the embodiment, but other type detectors as a camera tube, a solid state image sensor, or a position sensitive device may be used.

In the embodiments heretofore described, a three-dimensional magnetic position sensor with a resolution ability of 0.1 mm is used as the eye-point sensor 101, but the viewing-position detection may be performed by other means as a ultra-sonic sensor, an image sensor, or an optical sensor, in the scope of the invention. Furthermore, the first and the second order differentiators may be replaced with a speed sensor and an acceleration sensor respectively; or, the second order differentiator 103 and its accompanying parts may be omitted, when there is only such a small time delay that it can be sufficiently compensated with the first order differentiation, namely the second term $f(t) \cdot T_{delay}$ in right side of the equation (1). And still more, the present invention can be applied in a stereoscopic display of other types than the lenticular type, on condition that parallactical images are presented separately in a right and left direction to an observer, as a parallax barrier system for example, irrespective of difference of project type or straight looking type.

What is claimed is:

1. A viewing-position tracking stereoscopic-display having means for separately presenting right and left eye images to an observer, a viewing-position sensor for detecting a viewing-position of the observer, and a viewing-position tracker for controlling the means for presenting the eye images responsive to an output of the viewing-position sensor for representing a stereoscopic-view to the observer whenever the viewing-position moves; comprising:

means for obtaining a first order differentiation of positional information of the viewing-position of the observer to be used for controlling the viewing-position tracker;

means for obtaining a second order differentiation of positional information of the viewing-position of the observer detected by the viewing-position sensor; and the first order differentiation being used together with the second order said second order differentiation has been multiplied by a half square of the delay time.

2. A viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

means for obtaining a first order differentiation and a second order differentiation of positional information of the viewing-position of the observer detected by the viewing-position sensor; and means for obtaining compensated positional information for use in controlling the viewing-position tracker by adding said first order differentiation after being multiplied by a delay time occurring in the viewing-position tracking stereoscopic-display and said second order differentiation after being multiplied by a half square of said delay time to said positional information.

3. A method of viewing-position tracking applied in a viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

a step for obtaining first order differentiation and a second order differentiation of positional information of the viewing-position of the observer as detected by the viewing-position sensor;

a step for multiplying said first order differentiation by a delay time occurring in the viewing-position tracking stereoscopic-display and said second order differentiation by a half square of said delay time; and a step for viewing-position tracking in order so control the viewing-position tracker responsive to said positional information compensated by adding said first order differentiation multiplied by said delay time and said second order differentiation multiplied by said half square of said delay time.

4. A viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

means for obtaining a first order differentiation and a second order differentiation of positional information of the viewing-position of the observer detected by the viewing-position sensor; and means for obtaining compensated positional information of the viewing-position by adding said first order differentiation after being multiplied by a delay time occurring in the viewing-position tracking stereoscopic-display and said second order differentiation after being multiplied by a half square of said delay time to said positional information for a feedback controlling of the viewing-position tracker.

5. A viewing-position tracking stereoscopic-display having means for separately presenting right and left eye images to an observer, a viewing-position sensor for detecting a viewing-position of the observer, and a viewing-position tracker for controlling the means for presenting in response to an output of the viewing-position sensor for representing a stereoscopic-view to the observer whenever the viewing-position moves; comprising:

means for obtaining a first order differentiation and a second order differentiation of positional information of the viewing-position of the observer detected by the viewing-position sensor;

means for obtaining compensated positional information for use in controlling the viewing-position tracker by adding said first order differentiation after being multiplied by a delay time occurring in the viewing-position tracking stereoscopic-display and said second order differentiation after being multiplied by a half square of said delay time to said positional information; and means for revising a tracking error of the viewing-position tracker by comparing said positional information of the viewing-position of the observer with positional information fed-back from the viewing-position tracker.

6. A method of viewing-position tracking applied in a viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

a step for obtaining a first order differentiation and a second order differentiation of positional information of the viewing-position of the observer detected by the viewing-position sensor;

a step for multiplying said first order differentiation by a delay time occurring in the viewing-position tracking stereoscopic-display and said second order differentiation by a half square of said delay time;

a step for obtaining a tracking error of the viewing-position tracker by comparing said positional information of the viewing-position of the observer with positional information feedback from the viewing-position tracker; and a step for viewing-position tracking by controlling the viewing-position tracker responsive to said positional information of the viewing-position of the observer compensated with a value calculated from said first order differentiation multiplied by said delay time, said second order differentiation multiplied by said half square of said delay time, and said tracking error.

7. A viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

means for obtaining a first order differentiation and a second order differentiation of positional information of the viewing-position of the observer detected by the viewing-position sensor;

means for obtaining compensated positional information for use in controlling the viewing-position tracker by adding said first order differentiation after being multiplied by a delay time occurring in the viewing-position tracking stereoscopic-display and said second order differentiation after being multiplied by a half square of said delay time to said positional information; and means for revising a tracking error of the viewing-position tracker by feeding back information of luminous intensity distribution of said right and left eye images detected at the viewing-position of the observer.

8. A viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing position sensor for representing a stereoscopic-view to the observer whenever the viewing-position moves; comprising:

means for obtaining a first order differentiation and a second order differentiation of positional information of the viewing-position of the observer detected by the viewing-position sensor;

means for obtaining compensated positional information for use in controlling the viewing-position tracker by adding said first order differentiation after being multiplied by a delay time occurring in the viewing-position tracking stereoscopic-display and said second order differentiation after being multiplied by a half square of said delay time to said positional information; and means for revising a tracking error of the viewing-position tracker according to information of luminous intensity distribution of said right and left eye images detected at the viewing-position of the observer.

9. A method of viewing-position tracking applied in a viewing-position tracking stereoscopic-display having means for separately presenting right and left eye images to an observer, a viewing-position sensor for detecting a viewing-position of the observer, and a viewing-position tracker for controlling the means for presenting responsive to an output of the viewing-position sensor for representing a stereoscopic-view to the observer whenever the viewing-position moves; comprising:

a step for obtaining a first order differentiation and a second order differentiation of positional information of the viewing-position of the observer detected by the reviewing-position sensor;

a step for multiplying said first order differentiation by a delay time occurring in the viewing-position tracking stereoscopic-display and said second order differentiation by a half square of said delay time;

a step for obtaining a tracking error of the viewing-position tracker by feeding back information of luminous intensity distribution of said right and left eye images detected at the viewing-position of the observer; and a step for viewing-position tracking by controlling the viewing-position tracker responsive to said positional information of the viewing-position of the observer compensated with a value calculated from said first order differentiation multiplied by said delay time, said second order differentiation multiplied by said half square of said delay time, and said tracking error.

* * * * *